(12) United States Patent
Osborne et al.

(10) Patent No.: US 7,896,888 B2
(45) Date of Patent: Mar. 1, 2011

(54) MULTIPLE WIRE GUIDE INTRODUCER SYSTEM

(75) Inventors: Thomas A. Osborne, Bloomington, IN (US); Brian L. Bates, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 483 days.

(21) Appl. No.: 11/971,364

(22) Filed: Jan. 9, 2008

(65) Prior Publication Data
US 2008/0172064 A1 Jul. 17, 2008

Related U.S. Application Data

(60) Provisional application No. 60/880,903, filed on Jan. 17, 2007.

(51) Int. Cl.
*A61F 11/00* (2006.01)
(52) U.S. Cl. ................................ 606/108
(58) Field of Classification Search .......... 606/108, 606/191, 194; 604/164.01–164.09, 164.13, 604/170.01–170.03, 103.04, 171, 510, 528, 604/532; 600/585; 27/24.1
See application file for complete search history.

(56) References Cited

U.S. PATENT DOCUMENTS

| | | | | |
|---|---|---|---|---|
| 2,118,631 A | * | 5/1938 | Wappler | 604/170.02 |
| 4,405,314 A | * | 9/1983 | Cope | 604/510 |
| 4,798,193 A | * | 1/1989 | Giesy et al. | 600/114 |
| 4,931,037 A | * | 6/1990 | Wetterman | 604/8 |
| 5,549,563 A | * | 8/1996 | Kronner | 604/170.03 |
| 5,749,370 A | * | 5/1998 | Brooks et al. | 600/585 |
| 2002/0099309 A1 | * | 7/2002 | Beger et al. | 600/585 |
| 2003/0093039 A1 | * | 5/2003 | Sirhan | 604/284 |
| 2003/0149444 A1 | * | 8/2003 | Khaw | 606/194 |
| 2006/0200168 A1 | * | 9/2006 | Anwar et al. | 606/108 |

* cited by examiner

*Primary Examiner*—Anhtuan T Nguyen
*Assistant Examiner*—David Eastwood
(74) *Attorney, Agent, or Firm*—Brinks Hofer Gilson & Lione

(57) ABSTRACT

An introducer system for introducing a plurality of wire guides into a vessel of a patient includes first and second wire guides, and a catheter. The first wire guide has a curved proximal end, and a distal end sufficiently flexible for passage through the vessel to a target site for the procedure. The catheter has proximal and distal open ends, and a lumen extending therebetween. At least the distal end of the catheter has sufficient flexibility for passage over the first wire guide to the target site, and has an inwardly curved portion between the proximal and distal open ends. The catheter further has a side port proximally positioned along the inwardly curved portion. The side port is sized and arranged such that the curve of the first wire guide proximal end is passable therethrough when the catheter is passed over the first wire guide. The second wire guide is sized for passage through the lumen when the first wire guide is positioned in the lumen. The second wire guide has a stiffness greater than the stiffness of the first wire guide.

10 Claims, 4 Drawing Sheets

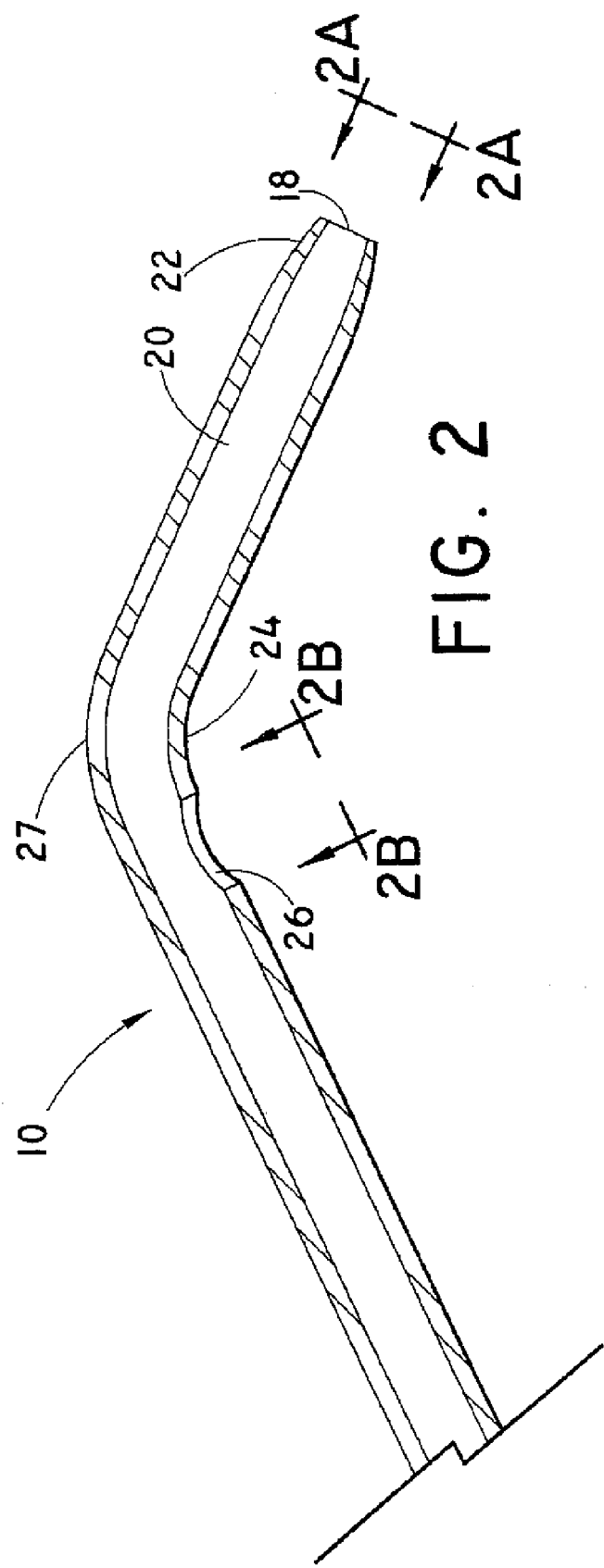

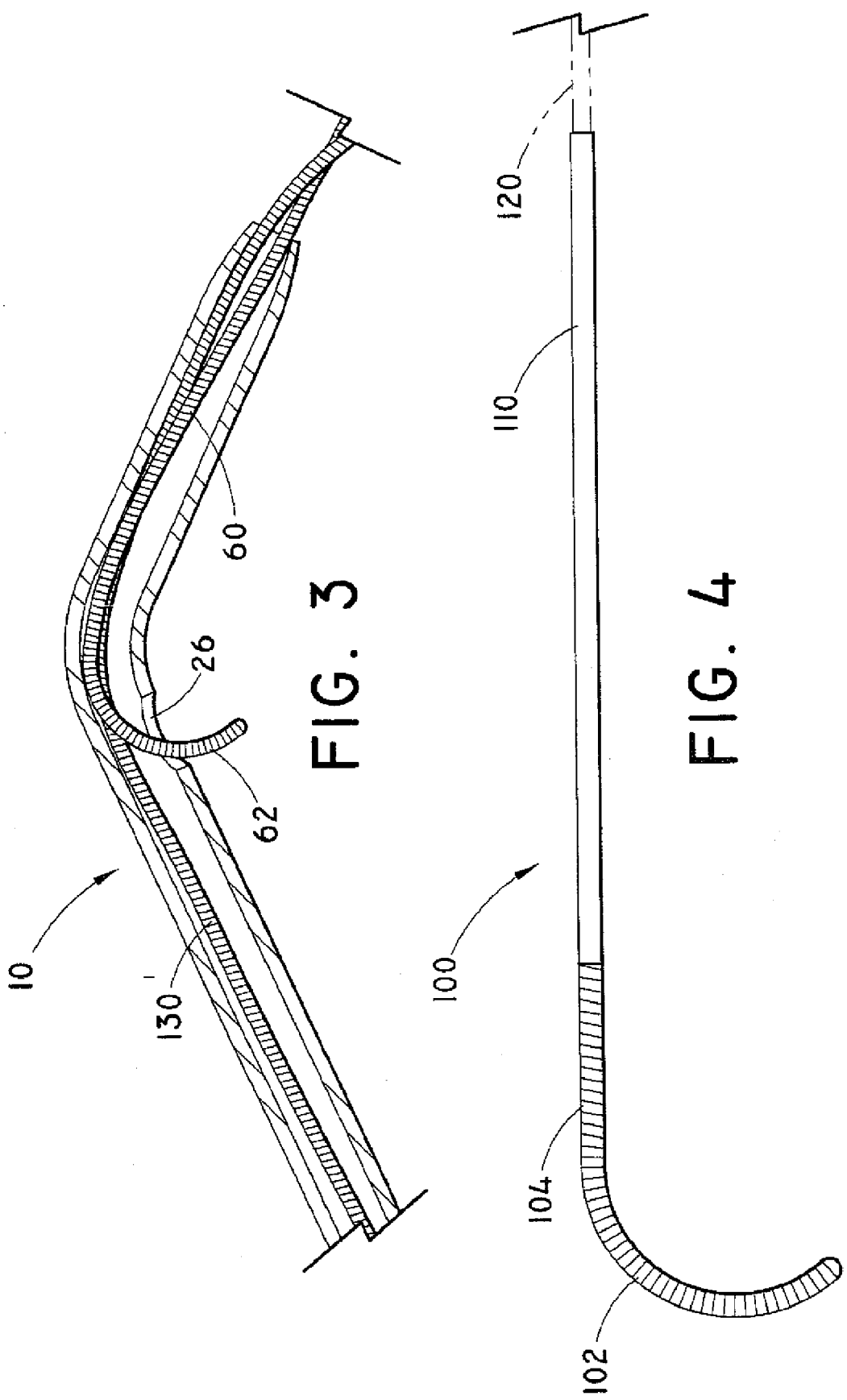

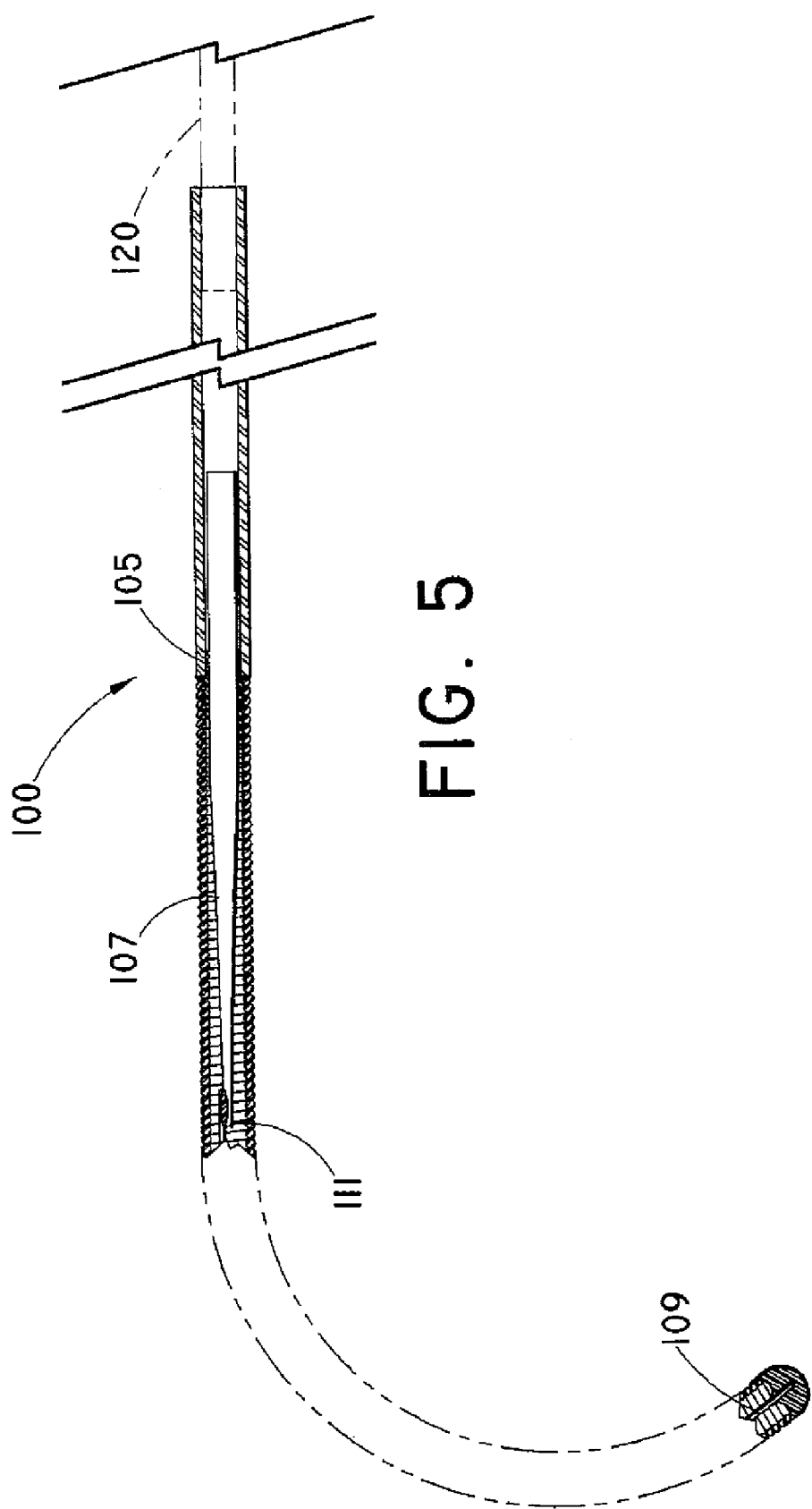

MULTIPLE WIRE GUIDE INTRODUCER SYSTEM

RELATED APPLICATION

The present patent document claims the benefit of the filing date under 35 U.S.C. §119(e) of Provisional U.S. Patent Application Ser. No. 60/880,903, filed Jan. 17, 2007, which is hereby incorporated by reference.

BACKGROUND

1. Technical Field

The present invention relates generally to a system for carrying out a medical procedure, and more specifically, to a system for carrying out a diagnostic or therapeutic procedure that utilizes two or more wire guides having different properties.

2. Background Information

In modern medicine, vascular procedures are frequently carried out by introducing a wire guide into a vessel, and directing the wire guide through the vessel to a target area for the procedure. Such wire guides are typically introduced into the vessel by well-known procedures, such as the Seldinger percutaneous access technique. The wire guide to be introduced will ideally have a suitable combination of flexibility and stiffness that allows it to be directed to the area of interest.

Introducing a wire guide in this manner can be relatively straightforward if the target area is situated in a portion of the vasculature that is not difficult to reach. However, it is often necessary to traverse tortuous areas of the vessel, and/or to cross one or more lesions in the vessel in order to reach the target area. In such cases, directing the wire guide to the target area can be a very time consuming and painstaking procedure, if it can be accomplished at all. Generally, the wire guide to be inserted is fairly "floppy", or flexible, in order to optimize the chances for successful positioning.

Although such wire guides are beneficial for purposes of traversing the tortuous areas of the vasculature, a highly flexible wire guide will often not be well suited for carrying out successive steps in the medical procedure. For example, in some diagnostic and interventional procedures, such as angioplasty and various stenting operations, a catheter is introduced over the wire guide and directed toward the area of interest. However, highly flexible wire guides often do not have sufficient stiffness to allow the catheter to track the wire guide through the vessel. As a result, the catheter may disturb or displace the distal tip of the wire guide away from the area of interest. This results in the need to exchange the first wire guide for a second, stiffer, wire that has sufficient strength to control the catheter.

The conventional approach to this wire exchange involves advancing the catheter as far as possible along the first wire, withdrawing the first wire, and advancing a second, stiffer, wire in its place through the vessel. However, this process results in the loss of the original wire placement. As a result, the physician must re-access the area of interest with a stiffer wire that is more difficult to advance into the tortuosity and/or lesion area. This process is time consuming, if possible at all, and exposes the patient to increased risk of failure.

Accordingly, there exists a need for a system and method that will allow for placement of a catheter and related devices in a vessel over a second wire guide, in a manner that does not sacrifice the original access and/or placement achieved by the first wire guide.

BRIEF SUMMARY

The present invention addresses the problems of the prior art. In one form thereof, the invention comprises an introducer system for introducing a plurality of wire guides into a vessel of a patient for carrying out a medical procedure. The introducer system comprises first and second wire guides, and a catheter. The first wire guide has a curved proximal end, and has a distal end having sufficient flexibility for passage through the vessel to a target site for the procedure. The catheter has proximal and distal open ends, and a lumen extending therebetween. At least the distal end of the catheter has sufficient flexibility for passage over the first wire guide to the target site, and has an inwardly curved portion between the proximal and distal open ends. The catheter further has a side port proximally positioned along the inwardly curved portion. The side port is sized and arranged such that the curve of the first wire guide proximal end is passable therethrough when the catheter is passed over the first wire guide. The second wire guide is sized for passage through the lumen when the first wire guide is positioned in the catheter lumen. Preferably, the second wire guide has a stiffness greater than the stiffness of the first wire guide.

In another form thereof, the invention comprises a method for inserting a plurality of wire guides into the body of a patient for carrying out a medical procedure. First and second wire guides are provided. The first wire guide has a curved proximal end, and the second wire guide has a greater stiffness than the stiffness of the first wire guide. The distal end of the first wire guide is inserted into an opening in a body vessel, and advanced through the vessel to a target site. A catheter having proximal and distal open ends and a lumen extending therebetween is provided. The catheter has sufficient flexibility for passage over the first wire guide to the target site, and has an inwardly curved portion between the proximal and distal open ends. The catheter further has a side port proximally positioned along the inwardly curved portion. The curved proximal end of the first wire guide is inserted into the distal end of the catheter, and the catheter is advanced relative to the first wire guide in a manner such that the first wire guide curve emerges through the side port. The catheter is further advanced along the first wire guide to the target site. The second wire guide is inserted into the proximal open end of the catheter, and advanced through the catheter lumen to the target site. The catheter may then be withdrawn from the vessel, followed by withdrawal of one of the wire guides, leaving the desired wire guide in place.

BRIEF DESCRIPTION OF THE DRAWINGS

FIG. 2 is an enlarged cross-sectional view of the distal tip section of the catheter of FIG. 1;

FIG. 2A is an end view of the catheter of FIG. 2;

FIG. 2B is an enlarged fragmentary view of the catheter of FIG. 2, illustrating one example of the configuration of the side port;

FIG. 3 is an enlarged cross-sectional view of the distal tip section of the catheter similar to that of FIG. 2, illustrating the presence of two wire guides in the lumen of the catheter;

FIG. 4 illustrates a wire guide extender according to an embodiment of the present invention; and FIG. 5 illustrates an enlarged cross-sectional view of a portion of the wire guide extender of FIG. 4.

DETAILED DESCRIPTION OF THE DRAWINGS AND THE PRESENTLY PREFERRED EMBODIMENTS

Figure 1:
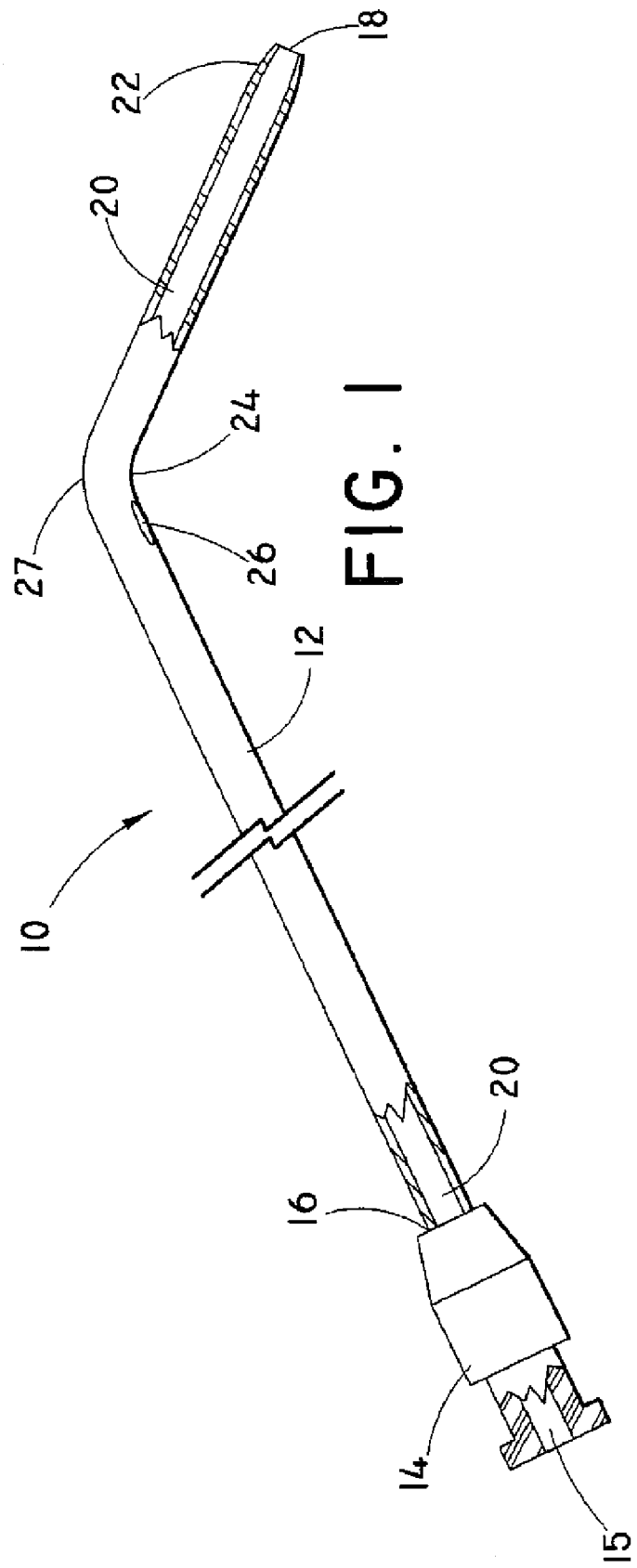
FIG. 1 is a side view of a catheter of a type that may be used in the inventive system according to one embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of respective components of the inventive system. The term "proximal" is used in its conventional sense to refer to the end of the component(s) that is closest to the operator during use. The term "distal" is used in its conventional sense to refer to the end of the component( s) that is initially inserted into the patient, or that is closest to the patient during use.

FIG. 1 illustrates a side view of a catheter 10 of a type that may be used in the inventive system. In the embodiment shown, catheter 10 includes a generally tubular catheter body 12, and a base portion 14 that is fitted for attachment to the proximal end of catheter body 12. Catheter body 12 has open proximal end 16 and distal end 18, and has a lumen 20 extending therebetween. Base portion 14 facilitates the grasping and manipulating of catheter 10, and includes a center passageway 15 that communicates with lumen 20 of catheter body 12. If desired, base portion 14 may also be structured to include one or more portals (not shown) for engagement with routine medical instrumentation in well known fashion.

Catheter body 12 has an externally tapered portion 22 that tapers in the direction of distal end 18. Preferably, open distal end 18 has a diameter sufficient to accommodate two wire guides in a side by side configuration, as shown in FIG. 3 and described in greater detail herein. This diameter allows two wires to be anchored at the area of interest, thereby providing the operator with the ability to choose between the two wires for use in the procedure. In a preferred embodiment, open distal end 18 has an oval shape, as shown in FIG. 2A, having a major diameter, e.g., of about 0.028 inch and a minor diameter of about 0.014 inch. Those skilled in the art will appreciate that the open distal end may have other geometrical configurations, such as round, and that the end dimensions may be varied depending upon the respective diameters of the wires that are intended to be passed therethrough. Catheter body 12 preferably has an outer diameter of between about 3 and 4 French, and a length of between about 100 and 180 cm. All dimensions provided herein are exemplary only, and those skilled in the art will appreciate that larger, or smaller, dimensions may be appropriate for a particular application.

As shown in FIGS. 1-3, catheter body 12 is inwardly curved along a portion of its length. Preferably, catheter body 12 has a gentle curve as illustrated, although other arrangements may be substituted. One non-limiting example of a gently curved configuration would be one having a curvature between about 110 and 170 degrees, preferably between about 130 and 140 degrees. A radius of curvature could, for example, be between 2 and 20 mm. Those skilled in the art will appreciate that these dimensions are also exemplary only, and that other dimensions may be substituted for a particular application, all of which are considered within the scope of the invention. Although the curve may be provided anywhere along the length of the catheter body, it is preferred that the curve be provided at the distal end of the catheter body, and more preferably, between about 2 and 15 cm from open distal end 18.

A side port 26 is located proximal to a midpoint 27 of the curve, and is positioned along the inner surface of the curve. Preferably, side port 26 is in closely spaced relationship with midpoint 27. By "closely spaced relationship" is meant that the side port is located just proximal to the curve midpoint, e.g., between about 0 and 10 mm proximal of midpoint 27 along a length of catheter body 12. Although it is preferred to position side port 26 in closely spaced relationship to the midpoint as described, alternate positions along the inner surface of the proximal curve may be substituted. Side port 26 is sized to permit passage therethrough of the proximal end 62 of a curved wire guide 60, as shown in FIG. 3. Preferably, side port 26 has an oval or elliptical shape as shown in FIG. 2B, with its long axis parallel to the longitudinal axis of catheter body 12. In a preferred embodiment, the side port dimension is about 2 to 3 times the diameter of the wire guide in the long axis, and about 1.5 times this diameter in the short axis.

Catheter systems that include a wire guide that is insertable into the distal end of the catheter and exits a side opening along the length of the catheter are known in the medical arts. Such catheter systems are commonly referred to as "rapid exchange" or "riding the rail" systems. Catheters of this type have a separate lumen or chamber that is open at the distal end and communicates with the side exit opening. An advantage of such catheters is that that they can be removed from an advanced position in the vascular system along the wire guide without requiring simultaneous removal of the wire guide. Thus, there is no need for a wire guide extension of the type that might otherwise be attached to the proximal end of the wire guide in an over-the-wire system to give the wire more length. However, providing the separate lumen or chamber in the catheter requires the inclusion of a septum or related structure at the distal portion of the catheter to define the extra lumen or chamber. The inclusion of the septum and the extra lumen or chamber significantly increases the overall diameter of the catheter, and also increases its stiffness.

To the contrary, catheter 10 of the inventive system is structured in a manner such that it does not require an additional lumen or chamber in order to cause a wire guide (as further described herein) that is inserted through the distal end of the catheter to exit through the side port 26. As a result, the catheter distal portion can be formed to have a very low profile and high flexibility, thereby facilitating advancement of the catheter to the target site at which the wire guide was initially placed.

Catheter body 12 is preferably formed of flexible material, such as plastic, having sufficient flexibility to enable the catheter to be directed through the tortuous pathways along the wire guide. Non-limiting examples of suitable materials for forming catheter body 12 include nylon, polyethylene, polyvinyl chloride (PVC) and polyfluoroethylenepropylene (PFEP). Those skilled in the art can readily select an appropriate catheter composition for a particular purpose, or intended use, of the catheter. Preferably, at least a portion of the length of catheter 10 is formed to be radiopaque, so that the position of the catheter can be monitored by x-ray fluoroscopy, or other suitable imaging device. Providing radiopacity to a catheter is very well known, and those skilled in the art can readily determine a suitable manner of adding radiopacity to the catheter of the present invention.

The inventive system also contemplates use of a wire guide having a curved proximal end. Preferably, the curve comprises a "J"-shape of the type that is well known in commercially available wire guides. However, when in use in the inventive system, the J-tip of a wire guide comprises the proximal end of the wire. With most J-tipped wire guides in common use, the J-tip comprises the distal end of the wire guide.

J-tipped wire guides suitable for use in the present invention are commercially available. Suitable wire guides may be obtained, e.g., from Cook Incorporated, of Bloomington, Ind., under the name SAFE T J wire. Suitable wires are typically about 90 to 180 cm length. The J-curve is typically curved through an arc of at least about 90 to 100 degrees, and preferably about 180 degrees. The radius of the curve is preferably between 1.5 and 20 mm, more preferably about 3 mm.

Although suitable J-tipped wire guides, such as wire guide 60, are commercially available, an advantage of the present invention is that specially purchased wire guides need not necessarily be utilized. Rather, virtually any conventional "straight" wire guide sized for passage to the target area can be adapted for use in the inventive system. In such case, a J-shaped extender or adapter may simply be engaged with the proximal end of the conventional wire guide. One such extender 100 is shown in FIGS. 4 and 5.

In the non-limiting embodiment shown, extender 100 has a J-shaped curved proximal end 102. Preferably, extender 100 comprises a length of small gauge thin-wall tubing 110 having an inside diameter sufficiently large such that the proximal end of a conventional wire guide 120 is snugly receivable therein. Wire guide 120 is shown in phantom in FIGS. 4 and 5. By "snugly receivable therein" is meant that the outer diameter of the wire guide end and the inner diameter of the needle tubing are virtually the same, or that the inner diameter of the tubing just slightly exceeds the outer diameter of the wire such that the wire end is snugly, but removably, received therein. In one non-limiting example, 23 gauge thin-wall tubing may be utilized to receive a wire guide of 0.014 inch outer diameter. As another alternative, 22 gauge thin-wall tubing can be used with 0.018 inch diameter wire guides. Those skilled in the art can readily match tubing with a suitable wire guide when following the teachings of the present invention.

In the non-limiting example shown, curved end 102 comprises a tightly wrapped coiled segment. The J portion should be formed to be "springy", so that it can be straightened when inserted into the catheter, but will return to its original J-shape when unconstrained. A coil that is cold worked or deformed into a J shape is particularly appropriate. A typical J wire construction is shown in FIGS. 4 and 5. Those skilled in the art will appreciate, however, that other known wire constructions may be substituted. In the embodiment of FIG. 5, a stiffening mandrel 107 is positioned within the interior space of the extender. The stiffening mandrel is tapered for a smooth transition from stiff to floppy (distal to proximal), and the floppy tip 111 of the mandrel taper preferably terminates just short of the J curve. A small thin ribbon wire, or "safety" wire, 109 is preferably attached to the tip, or reduced diameter, end of the tapered stiffening mandrel, and extends substantially to the tip of the J. This safety wire prevents the coils of the J from stretching or separating during withdrawal. A typical spacing of the portions of the J curve from the main body of extender 100 is preferably about 3 to 5 mm. The distal portion of curved end 102 is affixed to the proximal end of thin-wall tubing 110 by any conventional fastening means, such as by a solder/weld joint 105.

The following example describes one possible use of the inventive introducer system. In this example, the introducer system is utilized for gaining entry to a coronary artery through the coronary ostium. Initial entry to the vascular system may be made by any conventional technique, such as the well-known Seldinger percutaneous entry technique. In this technique, a puncture is made through a suitable artery, such as the femoral artery. The initial puncture may be made with, e.g., a 23 to 18 gauge needle, having a length of about 7 cm. An introducer sheath is then inserted at the puncture site. A conventional guide catheter is then placed through the sheath, and advanced to the ostium of the coronary artery.

A wire guide 60 is then provided for threading through the guide catheter to the target area. As stated, the proximal end of the wire guide may comprise, for example, a standard J-tip 62. Alternatively, a conventional "straight" wire guide end having a curved extender, such as extender 100, extending from the proximal end of the wire may be substituted. The distal end of wire guide 60 is advanced through the guide catheter, and is carefully and steadily worked through the tortuosity and lesions in the coronary artery in well-known fashion until the target area is reached.

Once the distal end of wire guide 60 has traversed the target site the distal end of catheter 10 is introduced over the curved proximal end 62 of the J-tipped wire guide (or the curved extender of a straight wire guide). Although it may be necessary to temporarily straighten out at least a portion of the curve for entry into the distal end of catheter 10, the curved proximal end maintains a tendency to return to the curved configuration. Catheter 10 is then advanced relative to the wire guide. When the curve 62 on the proximal end of the wire guide and the curve on the catheter 10 are at or near the same proximity, the respective curves align with each other. Once this "alignment" occurs, the tip of the J-curve will be on the inside of the curve, and will emerge through the side port 26 as the tip reaches this portion of the catheter. This is shown in FIG. 3. For optimal results, the radius of the J-curve will be at least slightly less than the radius of the curve in the catheter. The side port should be large enough, and shaped, such that the wire can emerge therethrough at an angle. Catheter 10 is then further advanced into the artery over the wire (or rail) until it reaches the target site previously reached by the distal end of the wire guide.

The physician may now select a second wire guide 130 (FIG. 3) having different properties than wire guide 60, and advance second wire guide 130 through the lumen of catheter 10 to the target site. Wire guide 130 will have one or more properties different from those of wire guide 60. Typically, wire guide 130 will be stiffer than wire guide 60. At this time, catheter 10 can be withdrawn, leaving the physician with a choice of two wires over which an interventional catheter or other medical device can be advanced. Generally, the stiffer wire will be the most likely wire to be selected for further use.

On some occasions, the physician may not be satisfied with the stiffness of either of the inserted wires, and may desire to replace one of these wires (typically the second wire) with yet another wire guide having properties (such as stiffness) different from the properties of the first and second wire guides. The inventive system advantageously provides the physician with the option of easily replacing a previously inserted and positioned wire guide with yet another wire guide that is believed to more optimally allow advancement of the interventional or diagnostic catheter or other device. In this event, catheter 10 can be easily re-inserted over wires 60, 130 in the same manner as originally introduced, advanced to the area of interest, and a third wire can be exchanged for the second wire 130. Based upon the desires of the physician, the replacement wire may be stiffer, or more flexible, than the wire that it replaces.

It is therefore intended that the foregoing detailed description be regarded as illustrative rather than limiting, and that it be understood that it is the following claims, including all equivalents, that are intended to define the spirit and scope of this invention.

The invention claimed is:

1. A method for inserting a plurality of wire guides into the body of a patient for carrying out a medical procedure, comprising:

providing a first wire guide having a proximal end and a distal end, said proximal end defining a curve; and providing a second wire guide, said second wire guide having a greater stiffness than a stiffness of the first wire guide;

inserting said first wire guide distal end into an opening in a body vessel, and advancing said wire guide distal end through said vessel to a target site;

providing a catheter having proximal and distal open ends and a lumen extending therebetween, said catheter having a flexibility sufficient for passage over said first wire guide to said target site, and having an inwardly curved portion between said proximal and distal open ends, said catheter further having a side port positioned proximal of a bend along said inwardly curved portion;

inserting the curved proximal end of the first wire guide into the catheter lumen through the distal end of said catheter, and advancing said catheter relative to the first wire guide in a manner such that said first wire guide curve emerges through said side port;

further advancing said catheter along said first wire guide to said target site; and inserting said second wire guide into the catheter lumen through the proximal open end of the catheter, and advancing said second wire guide through the catheter lumen to said target site.

2. The method of claim 1, further comprising the step of withdrawing the catheter from said vessel.

3. The method of claim 2, further comprising the steps of reinserting the proximal end of the first and second wire guides into the distal end of said catheter, advancing said catheter over said first and second wire guides in a manner such that said first wire guide curve emerges through said side port, and further advancing said catheter along said first and second wire guides to said target site;

withdrawing said second wire guide; and inserting a third wire guide into the proximal open end of the catheter, and advancing said third wire guide through the catheter lumen to said target site, said third wire guide having a stiffness that differs from the stiffness of the second wire guide.

4. The method of claim 2, further comprising the step of withdrawing the first wire guide from the vessel.

5. The method of claim 1, wherein said proximal end curve of said first wire guide comprises a J-shape.

6. The method of claim 1, wherein said first wire guide comprises an initially separate elongated wire and an extender portion, said extender portion comprising said curve, and being engaged with a proximal end of said elongated wire.

7. The method of claim 6, wherein said extender portion comprises a tubular member having a proximal end and a distal end, said distal end sized for snugly receiving said elongated wire proximal end, said curve engaged with said proximal end of said tubular member.

8. The method of claim 1, wherein said inwardly curved portion of said catheter is located closer to said catheter distal end than to said catheter proximal end, and wherein said side port is positioned in closely spaced relationship with said bend of said inwardly curved portion.

9. The method of claim 8, wherein said inwardly curved portion of said catheter has a curvature between about 110 and 170 degrees.

10. The method of claim 1, wherein said catheter tapers toward said distal open end, said distal open end having a diameter sufficient to accommodate said first and second wire guides in side-by-side relationship.

* * * * *